(12) United States Patent
Brandao

(10) Patent No.: US 11,191,626 B1
(45) Date of Patent: Dec. 7, 2021

(54) TAG BASED ADMINISTRATION OF PHARMACEUTICAL AGENTS TO LIVESTOCK

(71) Applicant: HerdDogg, Inc., Ashland, OR (US)

(72) Inventor: Melissa Brandao, Laramie, WY (US)

(*) Notice: Subject to any disclaimer, the term of this patent is extended or adjusted under 35 U.S.C. 154(b) by 0 days.

(21) Appl. No.: 17/248,590

(22) Filed: Jan. 29, 2021

Related U.S. Application Data

(60) Provisional application No. 62/706,433, filed on Aug. 17, 2020.

(51) Int. Cl.
| | |
|---|---|
| *A01K 29/00* | (2006.01) |
| *A61D 7/00* | (2006.01) |
| *A61M 37/00* | (2006.01) |
| *A01K 13/00* | (2006.01) |
| *A01K 11/00* | (2006.01) |

(52) U.S. Cl.
CPC ............. *A61D 7/00* (2013.01); *A01K 11/001* (2013.01); *A01K 13/003* (2013.01); *A61M 37/0069* (2013.01); *A61M 2205/0294* (2013.01); *A61M 2205/3306* (2013.01); *A61M 2205/3327* (2013.01); *A61M 2205/3368* (2013.01); *A61M 2205/3584* (2013.01); *A61M 2205/6018* (2013.01); *A61M 2210/0662* (2013.01); *A61M 2230/63* (2013.01); *A61M 2250/00* (2013.01)

(58) Field of Classification Search
CPC .. A01K 11/001; A01K 13/003; A01K 11/004; A01K 11/006; A01K 11/007; A01K 11/008; A01K 27/007; A61D 7/00; A61M 37/0069; A61M 2250/00
See application file for complete search history.

(56) References Cited

U.S. PATENT DOCUMENTS

| | | | | |
|---|---|---|---|---|
| 4,184,452 A | | 1/1980 | Buzzell et al. | |
| 4,506,630 A | * | 3/1985 | Hair ...................... | A01K 11/001 119/654 |
| 4,694,781 A | * | 9/1987 | Howe ................... | A01K 13/003 119/655 |
| 4,697,549 A | * | 10/1987 | Hair ...................... | A01K 11/001 119/651 |
| 4,878,456 A | * | 11/1989 | Howe ................... | A01K 11/001 119/653 |
| 4,885,855 A | * | 12/1989 | Marks, Sr. ........... | A01K 11/001 40/301 |

(Continued)

*Primary Examiner* — Trinh T Nguyen
(74) *Attorney, Agent, or Firm* — Hall Estill Law Firm

(57) ABSTRACT

Apparatus and method for autonomously administering a pharmaceutical agent, such as an insecticide, to an animal. A tag assembly is attached to the animal at a suitable location such as through an outer ear thereof. The tag assembly includes a reservoir to retain the pharmaceutical agent. An actuator of the tag assembly is configured to open the reservoir responsive to a control signal from a control circuit. An application mechanism facilitates a transfer of the pharmaceutical agent to the animal in response to the actuator. In some cases, the control signal may be transmitted to the tag assembly from an external source via a wireless connection. In other cases, the control signal may be generated internally using a sensor of the tag assembly. The tag assembly may include multiple reservoirs so that applications of the agent can be carried out at different times and under different conditions as required.

16 Claims, 9 Drawing Sheets

(56) References Cited

U.S. PATENT DOCUMENTS

| | | | |
|---|---|---|---|
| 5,016,369 A * | 5/1991 | Parry | A01K 13/003 |
| | | | 40/301 |
| 5,189,986 A | 3/1993 | Burkoth | |
| 5,280,768 A | 1/1994 | Galphin, Jr. | |
| 7,713,537 B2 | 5/2010 | Arther et al. | |
| 7,744,589 B2 | 6/2010 | Mounce et al. | |
| 7,988,702 B2 * | 8/2011 | Wendlandt | A61B 17/068 |
| | | | 606/151 |
| 8,956,635 B2 | 2/2015 | O'Hara et al. | |
| 9,591,830 B2 | 5/2017 | Hall | |
| 9,848,577 B1 | 12/2017 | Brandao et al. | |
| 10,130,265 B1 | 11/2018 | Brandao et al. | |
| 10,398,317 B2 | 9/2019 | Crider, Jr. et al. | |
| 2011/0184342 A1 | 7/2011 | Pescach | |
| 2012/0210630 A1 | 8/2012 | Ashley et al. | |
| 2014/0083367 A1* | 3/2014 | Kellerby | A01K 11/001 |
| | | | 119/651 |
| 2016/0120628 A1 | 5/2016 | Kapil | |
| 2019/0269120 A1 | 9/2019 | Bunker et al. | |
| 2020/0114064 A1 | 4/2020 | Reeves | |
| 2020/0164193 A1 | 5/2020 | Williams et al. | |

\* cited by examiner

TAG BASED ADMINISTRATION OF PHARMACEUTICAL AGENTS TO LIVESTOCK

RELATED APPLICATION

The present application makes a claim of domestic priority under 35 U.S.C. 119(e) to U.S. Provisional Patent Application No. 62/706,433 filed Aug. 17, 2020, the contents of which are hereby incorporated by reference.

BACKGROUND

Livestock management is generally concerned with the care and maintenance of livestock (e.g., domesticated animals such as cattle, sheep, swine, etc.) in an agricultural setting. Livestock management systems are usually implemented with a view toward the commercial production of commodities from such animals for human consumption and use.

Modern agricultural practices have increasingly incorporated the use of technology to assist in livestock management efforts. It is common for domesticated livestock animals such as cattle to wear or otherwise carry machine interactive tags that can be used to track the location and status of the individual animals in a particular setting, such as a dairy farm, feed lot, ranch, etc.

Data collection and analysis systems can aggregate tag data to enable a user to perform various livestock management tasks. For example, sensors affixed to the animals or located proximate congregating locations for the animals can collect various types of data such as temperature, geoposition, movement, methane production, etc. in order to determine useful information regarding the states of the animals.

While these and other existing technical solutions in the area of livestock management have been found operable, there remains a continued need for improvements in the art of livestock management. It is to these and other improvements that various embodiments of the present disclosure are directed.

SUMMARY

Various embodiments of the present disclosure are generally directed to an apparatus and method for autonomously administering a pharmaceutical agent, such as an insecticide, to an animal.

In some embodiments, a tag assembly is attached to the animal at a suitable location such as through an outer ear thereof. The tag assembly includes a reservoir to retain the pharmaceutical agent. An actuator within the tag assembly is configured to open the reservoir responsive to a control signal from a control circuit. An application mechanism facilitates a transfer of the pharmaceutical agent from the reservoir to the animal in response to the actuator. In some cases, the control signal may be transmitted to the tag assembly from an external source via a wireless connection. In other cases, the control signal may be generated internally using a sensor of the tag assembly. The tag assembly may include multiple reservoirs so that applications of the agent can be carried out at different times and under different conditions as required.

These and other features and advantages of various embodiments can be understood from a review of the following detailed description in conjunction with a review of the accompanying drawings.

DETAILED DESCRIPTION

Figure 1:
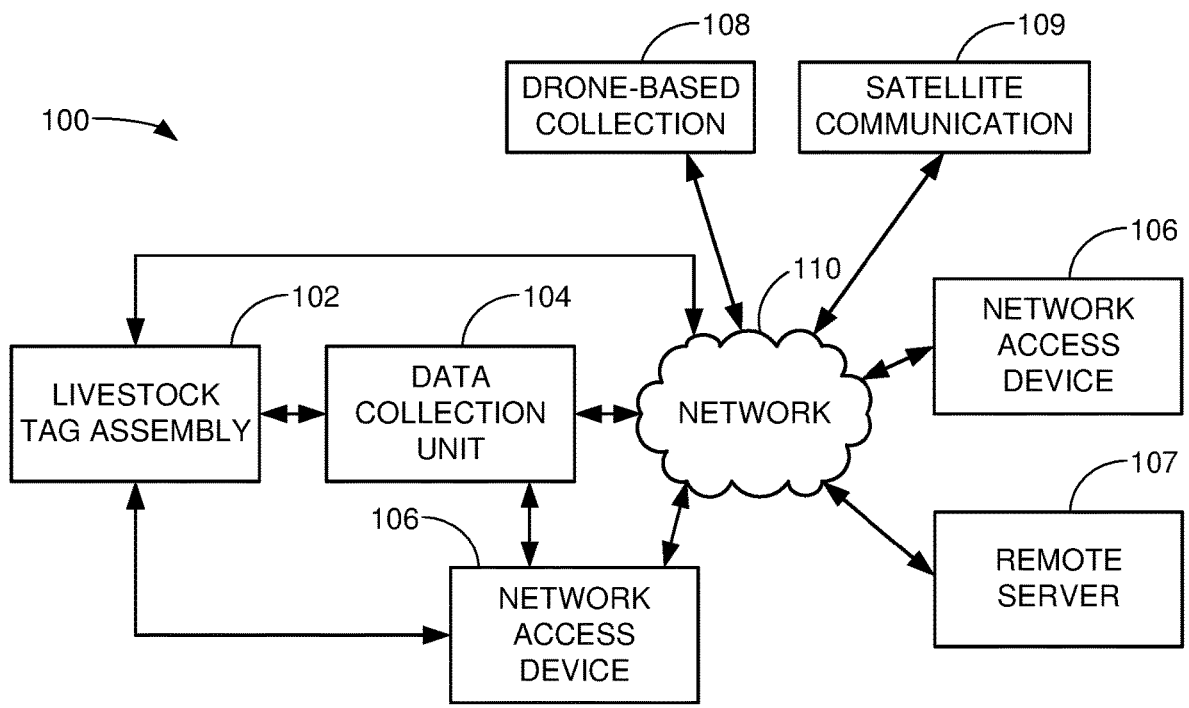
FIG. 1 is a functional block diagram for a livestock management system constructed and operated in accordance with various embodiments.

The present disclosure is generally directed to a tag based system for administering pharmaceutical agents (e.g., medicinal compounds) to livestock. The various embodiments discussed in detail herein are generally directed to systems for managing livestock, such as but not limited to cattle, in an agricultural setting. The systems, methods and devices set forth herein are not so limited, however, as other forms of domesticated and wild mammals may be managed using these techniques, including but not limited to wolves, large cats, deer, bison, goats, elephants, etc. Moreover, it will be immediately apparent that the various techniques disclosed herein can be applied to other forms of animals, including humans.

As explained below, some embodiments provide a tag assembly adapted to collect, receive and transmit data associated with a livestock animal, such as a cow. The tag assembly has a tag (base) which encloses various electronic components. In some cases, the tag assembly is characterized as an ear tag, so that an elongated shaft assembly extends from the tag to pierce and extend through an outer ear of an animal. A backing member is attachable to the distal end of the shaft assembly to retain the tag assembly to the ear.

The tag assembly can incorporate various sensors to provide an indication of a present state of the animal. These sensors can include, without limitation, temperature sensors, accelerometers, geoposition sensors, optical sensors, humidity sensors, methane sensors, proximity sensors, etc. Communication and control circuitry may further be implemented into the tag assembly to enable information to be transferred from the tag assembly to a remote device or server, as well as to enable information and commands to be issued to the tag assembly from a remote device or server.

In some embodiments, the tag is provided with a dispenser assembly configured to controllably dispense a pharmaceutical agent to the animal. One suitable agent may be an insecticide to reduce incidence of annoying and harmful insects upon the animal, such as mosquitos, flies, ticks, fleas, etc. For purposes of the present discussion, an insecticide is a material that discourages insects from landing, breeding, feeding, etc., regardless whether the material actually tends to cause the actual death of the insect. Hence, insect repellants, which may or may not result in the death of an insect, and true insecticides, such as certain types of nerve agents, etc. which do tend to result in death of an insect provided a sufficient concentration is applied to the insect, are both included in the definition of an insecticide for the present disclosure. Obviously, insecticide agents of whatever type should be applied in such a manner as to not induce harm to the animal to which the insecticide is applied.

While insecticides are of particular utility, other pharmaceutical agents besides insecticides can be applied, such as but not limited to vitamins or other dietary supplements, antibiotics, hormones, analgesics, steroids, antibiotics, etc. Substantially any beneficial compound can be injected or otherwise applied to the associated animal as desired, in such a manner that a beneficial result is obtained without causing an undue burden or injury to the animal, in accordance with the various embodiments disclosed herein.

The dispenser assembly can include one or more reservoirs in which selected quantities (volumes) of the pharmaceutical agent are retained. An actuator mechanism is supplied to act upon the reservoir, such as by rupturing a membrane or other reservoir barrier enclosing the agent. An application mechanism is provided to enable the released agent to be applied to the animal from the reservoir. In some cases, the agent may be topically applied so that the agent is spread to the dermis (skin) or other external layers of the animal, such as hair, down, etc. In other cases, the agent may be injected into the animal. The injected compound can be, without limitation, introduced into a dermal, subcutaneous (fat) and/or muscular layer of the animal. The injected compound can further be introduced intravenously (e.g., into a bloodstream) or into a tissue of the animal, as required.

The system is arranged such that a controlled amount of the pharmaceutical agent is administered to the animal in response to a control signal. The signal may be an external signal that is transmitted to the tag assembly from a remote device. In other embodiments, internal measurements of sensor data may enable the tag assembly to autonomously apply the agent without intervention from an external source, so that the signal is internally generated and used. In one embodiment, a tag assembly is provided with multiple reservoirs (doses) of an appropriate agent, allowing multiple administrations of the agent over time. The administration can be on an elapsed time basis (e.g., every two weeks over an eight week period), on an activity basis (e.g., based on sensor data that indicates the animal is highly agitated such as from insects), based on control data sent to the tag, etc. In further embodiments, a push system can be used such that a user of the system is notified of the status of the animal, and affirmatively confirms, such as via a user interface, that the administration should proceed (this can apply to all cases including the scheduled administration and sensor-based administration cases, as well as in other cases).

In this way, animals can receive administered medicinal agents based on tailored information associated with the individual animals, with no or minimal human intervention. There is no need to approach, disturb or otherwise physically interact with the animal (apart from wireless communications with the tag assembly) in order for the administration to take place. More generally, as desired the agent dispensing mechanism can be integrated into a larger, full traceability system in which full data are accumulated and verified regarding an animal over its useful lifecycle, including but not limited to geoposition data, health data, treatment data, etc.

These and other features and advantages of various embodiments can be understood beginning with a review of FIG. 1 which shows a functional block representation of a livestock management system 100. The system 100 includes a number of different modular components that can be utilized within the system as desired under different operational environments. Representative components include a livestock tag assembly 102, a data collection unit 104, a number of network access devices 106 and a remote server 107.

These various components can take a variety of configurations. In some embodiments, each tag assembly 102 will include control circuitry, communication circuitry, sensor circuitry and pharmaceutical agent dispensing mechanisms (discussed below). The data collection units 104 may include control circuitry, communication circuitry, and as required, sensor circuitry. While the tag assemblies are attached to the respective animals, the data collection units may be located in stationary or moveable locations to receive data from and communicate data to the tag assemblies.

The network accessible devices 106 may comprise portable or stationary communication systems that can interact with the tags, the data collection units and the network. Examples include but are not limited to smart phones, tablets, laptop computers, desktop computers, and other types of portable or stationary computer modules. In some cases, a user may approach and engage a communication session between the network accessible device 106 and one of the data collection units 104 to download and exchange accumulated information. One or more local applications (apps) may be loaded onto the network accessible device 106 to provide the user with a number of available functions to analyze data and make decisions/enact operations.

The remote server 107 may be located in a geographic location that is remote with respect to the herd/local users of the system. The server 107 can include processing, data storage and data analysis capabilities. Further elements shown in FIG. 1 include a drone-based collection system 108 and a satellite-based communication system 109. The network 110 can include any number of network communication systems including local, wide area, Internet and satellite-based communication systems that facilitate communications among the various components shown in FIG. 1.

The drone-based collection system 109 can be incorporated into an air-borne mobile platform that can be navigated in three-dimensional (3D) space near a herd of animals to collect and transmit data from and to the tag assemblies 102, the data collection units 104 and/or the network accessible devices 106. A local user can use the network accessible device 106, for example, to direct the drone-based collection system 108 to appropriate locations to provide data, telemetry, optical and other forms of data surveillance regarding the herd. The drone-based collection system 108 may be a battery powered drone with one or more propellers or other lift-generating systems to enable flight and maneuvering of the drone in a 3D space. The drone can be used for other purposes as well, such as herding, extraneous sensing, etc.

The satellite-based communication system 109 may be one of a constellation of communication satellites placed in orbit around the earth that facilitate communication among various elements of the system 100. This can be particularly useful in remote areas in which cellular coverage is not sufficiently available. Satellite-based data from the system 109 can also be used for a variety of applications useful to the present discussion, including weather monitoring, geotracking, etc.

Figure 2:
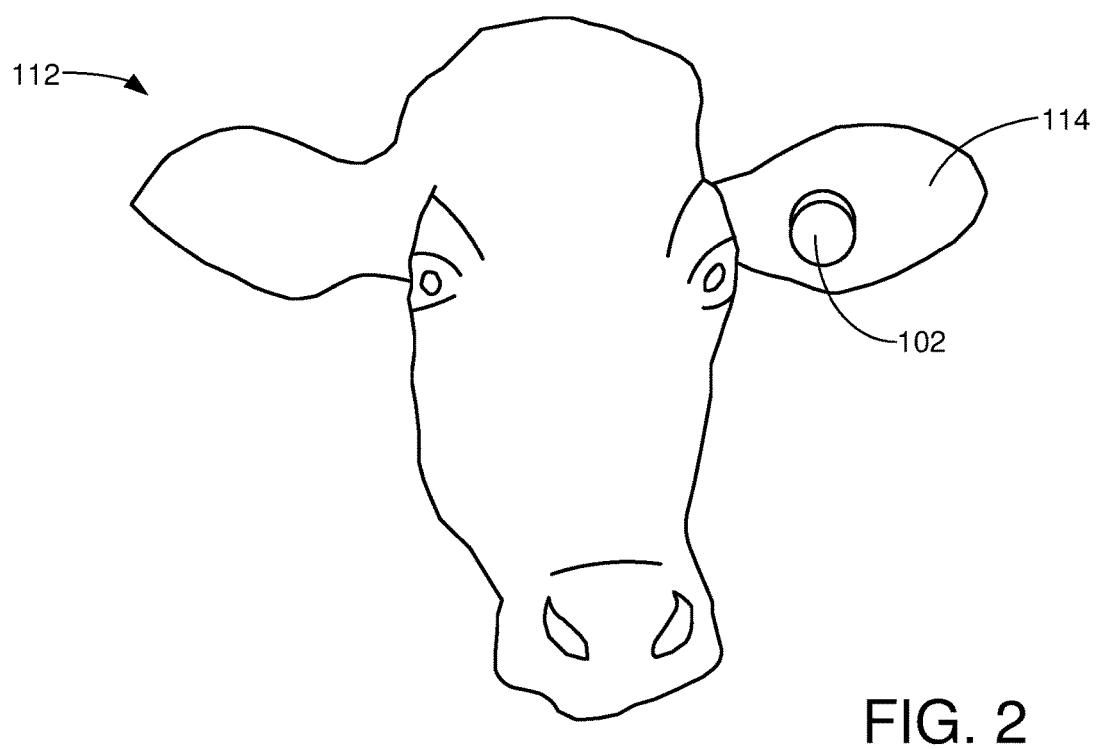
FIG. 2 is a schematic depiction of a cow having a tag assembly of the system of FIG. 1 in accordance with some embodiments.

FIG. 2 depicts the head of a livestock animal 112 (in this case, a cow) to illustrate an exemplary placement of the tag assembly 102 in a centered relation to an ear 114 of the cow. As noted above, while the various embodiments presented herein are particularly suitable for the management of a herd of cattle, the system can be readily adapted for use with substantially any type and/or group of animal, including domesticated or wild mammals. While the tag 102 in FIG. 2 is shown to be substantially disc-shaped, any suitable configuration, size, shape and style of tag can be adapted for use in accordance with the present discussion.

Figure 3:
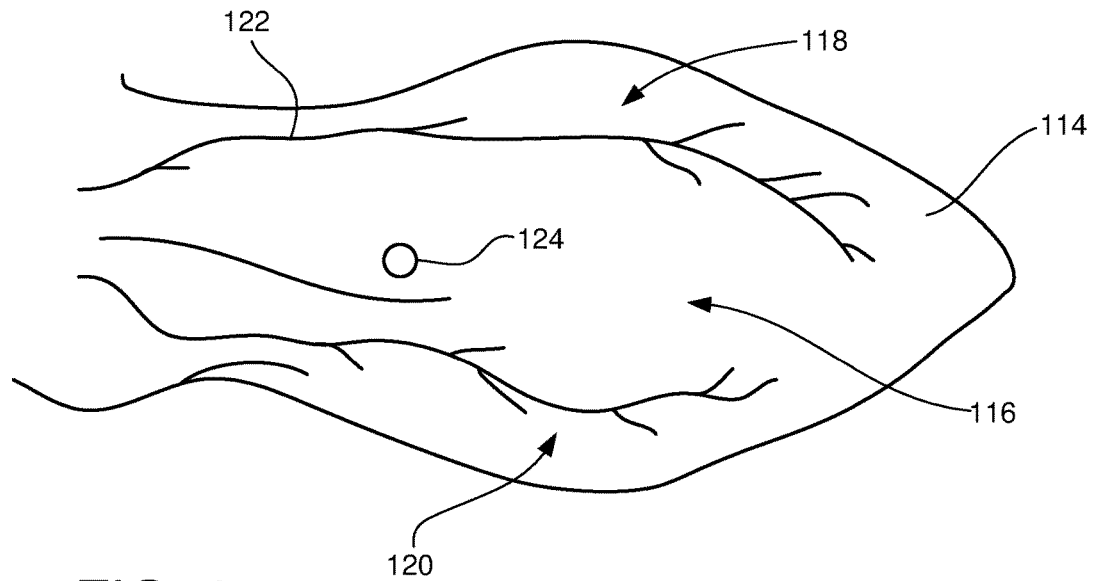
FIG. 3 is a schematic depiction of an ear of the cow from FIG. 2.

FIG. 3 represents a typical bovine ear schematic for the outer ear (auricle) 114 of the cow 112 from FIG. 2. A central cartilage region 116 is bounded by upper and lower vascular regions 118, 120 each having a network of blood vessels 122. Target location 124 represents a particularly suitable placement for the installation of tag assembly 102, although other locations may be selected. The target location 124 is just above the large blood supply provided by the lower vascular region 120. Other locations and arrangements can be used.

Figures 4A, 4B:
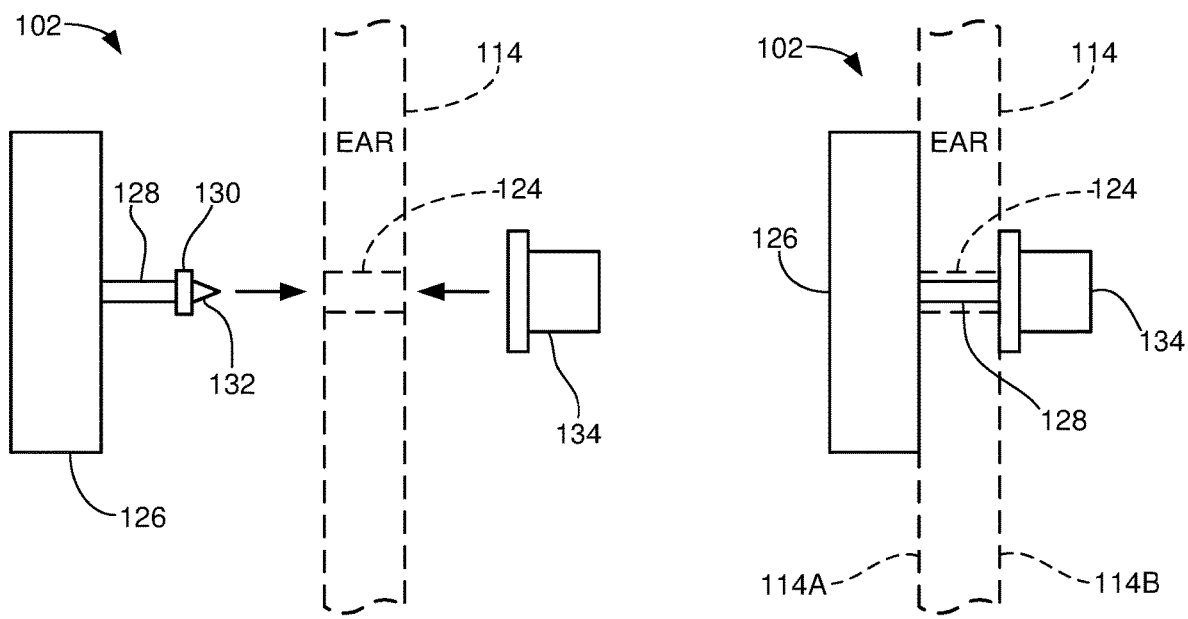
FIGS. 4A and 4B show an installation sequence for the tag assembly of FIG. 2 into the ear of FIG. 3.

FIG. 4A shows a side elevational depiction of the tag 102 and the ear 114 in some embodiments. The tag assembly 102 includes a main body 126, which as described above may be disc-shaped although such is merely exemplary and is not limiting. A shaft 128 extends from a medial location of the main body 126 and includes an annular retention flange 130 and tapered tip 132. These elements may be formed of metal, plastic or other suitably rigid material and are designed to pierce and extend through the animal's ear 114 as shown. A backing member 134 is configured to engage the flange 130 to temporarily or permanently secure the tag assembly 102 to the ear 114. FIG. 4B shows the tag assembly 102 in an installed configuration. It will be noted that both the main body 126 and the backing member 134 are generally brought into contact with opposing front and back surfaces 114A, 114B of the ear 114.

Figure 5:
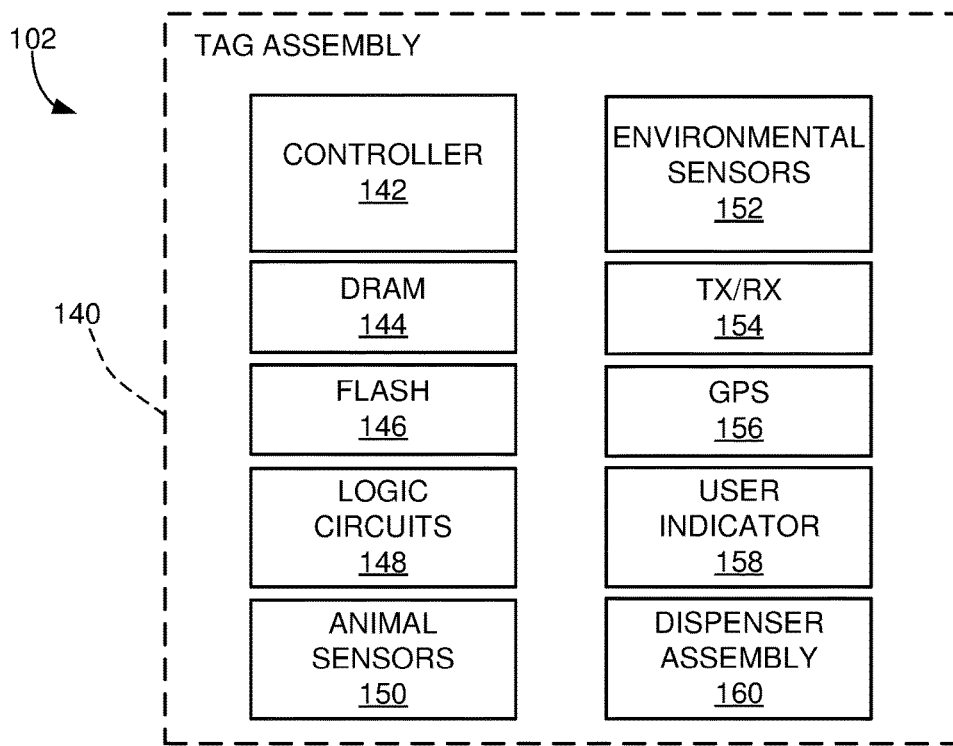
FIG. 5 is a functional block representation of the tag assembly in accordance with some embodiments.

FIG. 5 is a functional block representation of the tag assembly 102 in some embodiments. The main body 126 incorporates a housing 140 to enclose various electrical circuits and mechanical elements of interest. These include a controller 142, which provides top level control for the tag assembly 102. The controller 142 may be realized as one or more programmable processor circuits that utilize executable program instructions (e.g., firmware, software) stored in local memory. The firmware may be updated as required. Additionally or alternatively, the controller may be a non-processor based hardware circuit such as an application specific integrated circuit (ASIC), field programmable gate array (FPGA), logic circuitry, etc. The controller 142 and related circuitry may be incorporated into a system on chip (SOC) device.

Local memory for the controller 142 includes volatile memory such as DRAM 144 and non-volatile memory such as flash memory 146. Other memory and circuit configurations can be used. These respective memories may be used to accumulate measurement data, metadata and/or programming instructions, as well as any other data used by the device as required. A logic circuits block 148 represents other electrical elements including passive and active elements, gate logic, power regulators, switching devices, etc. used by the tag assembly.

A number of animal sensors are represented at 150. These sensors can take a number of forms such as temperature sensors, multi-axial accelerometers, humidity sensors, methane sensors, etc. A number of multi-range proximity environmental sensors 152 are used to provide different proximity environmental indications based on different distances of the animal from fixed locations. A transmitter/receiver (TX/RX) circuit 154 communicates data to and receives data from other communication devices such as those shown in FIG. 1. A global position system (GPS) circuit 156 can be used to provide geoposition data relating to the tag assembly 102. A user indicator circuit 158 operates to provide user indications associated with the tag. This can include circuitry used to activate an LED, apply audio/video/tactile indications, etc. In some cases, each tag assembly is provided with a unique ID value which allows the system to track each tag, and by extension each animal, and accumulate history data associated therewith.

Of particular interest to the present discussion is block 160, which represents a dispenser assembly 160. As explained below, the dispenser assembly 160 is configured to administer one or more pharmaceutical agents to the animal (e.g., the cow 112 in FIG. 2). These administrations may take place responsive to sensor readings supplied by the sensors 150, 152.

Figure 6:
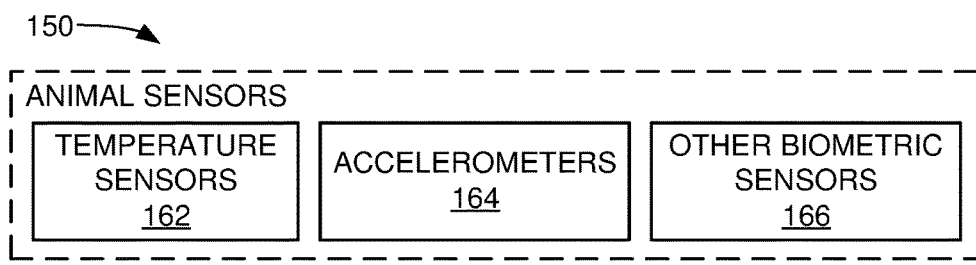
FIG. 6 is a functional block representation of the respective animal sensors from FIG. 5 in some embodiments.

To this end, FIG. 6 provides a functional block representation of the animal sensors 150 from FIG. 5 in some embodiments. Other arrangements can be used. The sensors include one or more temperature sensors 162, one or more accelerometers 164, and other biometric sensors 166. The temperature sensors can measure temperatures associated with the animal including a core body temperature, an outer ear temperature, an ambient temperature, etc. For example, in some embodiments the outer ear temperature can be established using a temperature sensor that is embedded in the tag shaft 128 or in facing relation to the inner or outer surfaces 114A, 114B of the ear 114.

The accelerometers may provide multi-axial (e.g., x, y, z) piezoelectric responses to motion by the animal's head, legs, body, etc. The other biometric sensors may include other animal body or ambient environmental sensor indications. In some cases, the sensors are all integrated into the housing 140 of the tag; in other cases, auxiliary sensors, such as sensors attached to other locations of the animal, ingested by the animal, etc. may be used. It will be appreciated that other sensor indications, such as the information provided from the environmental sensors 152, can also be incorporated into the analysis and operative functions of various embodiments.

Figure 7:
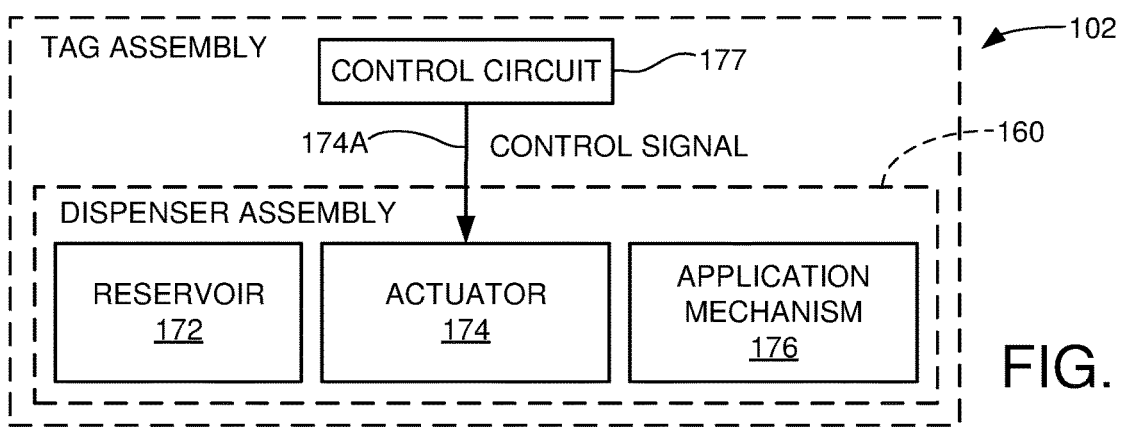
FIG. 7 is a functional block representation of the dispenser assembly from FIG. 5 in some embodiments.

The dispenser assembly 160 of the tag assembly 102 is shown in greater detail in FIG. 7. This assembly generally includes at least one reservoir 172, at least one actuator 174, and at least one application mechanism 176.

The reservoir 172 stores and retains an associated volume of a pharmaceutical agent. As noted above, the pharmaceutical agent can take any desired form, including but not limited to an insecticide, a hormone, an antibiotic, an nutritional supplement, a fluid, a steroid, a marker, etc.

The actuator 174 operates upon the associated reservoir to release the enclosed agent from an interior of the associated reservoir. It is contemplated in at least some cases that the actuator will apply a force, whether positive or negative, with respect to the associated reservoir to release the enclosed agent. A number of different configurations are discussed below, from passive means (e.g., the opening/release of a port/door) to active means (e.g., the application of force to press, puncture, squeeze, direct, vibrate, or otherwise operate upon a boundary of the reservoir). Regardless, each of these involve an action that opens the reservoir to permit release of the agent therefrom. The actuator 174 operates in response to the application of a control signal 174A from a control circuit 177, which may correspond to a control circuit such as the controller 142 (see FIG. 5).

The application mechanism 176 directs the released agent to move toward, onto and/or into the body of the associated animal. The application mechanism thus serves to transfer the released agent from the reservoir to the animal body. Various alternatives for the application mechanisms are discussed below including ports, syringes, etc.

The dispenser assembly 160 may operate in response to one or more of the animal sensors 150 in FIG. 6. In one illustrative embodiment, sensor indications that suggest the animal is engaging in behavior indicative of an annoyance (e.g., flies, mosquitoes, etc.) may be detected, resulting in the administration of a controlled dosage of a suitable agent (e.g., an insecticide) in order to relieve the condition of the animal. In another illustrative embodiment, other parameters, such as a time schedule, extraneous information, etc. may be used to schedule the administration of the various dosages of the pharmaceutical agent(s) to the animal.

Figure 8A:
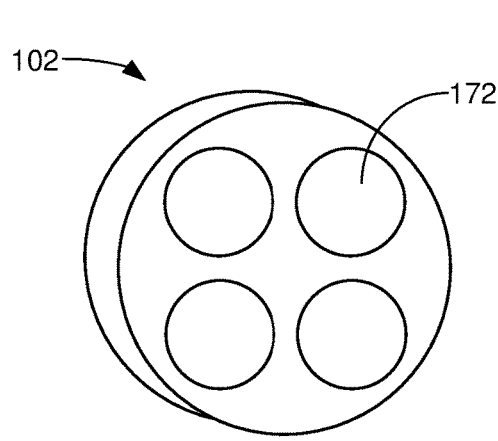
FIGS. 8A-8E illustrate different arrangements of the dispenser assembly in accordance with some embodiments.

FIGS. 8A-8D show different arrangements for the dispenser assembly 160 in accordance with some embodiments. Other configurations will readily occur to the skilled artisan in view of the present discussion. In FIG. 8A, a total of four (4) reservoirs 172 are provided in facing relation to the front ear surface 114A (FIG. 4B). Other numbers of reservoirs can be provided, including fewer than four or more than four, as required. While it is contemplated that each reservoir may store the same type of agent, in other embodiments, different types of agents may be separately stored and made available for administration to the animal as required. Moreover, different reservoirs may store the same type of pharmaceutical agent, but may store the same or different quantities (e.g., volumes) thereof.

Figure 8B:
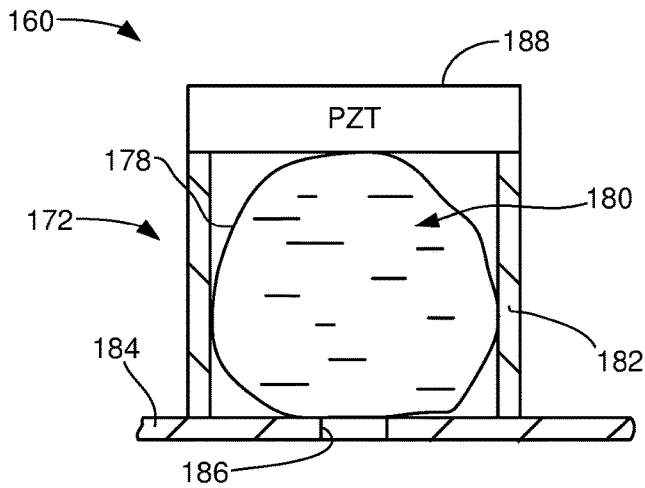

FIG. 8B shows a cross-sectional representation of the dispenser assembly 160 in some embodiments. The reservoir 172 is arranged as an enclosed membrane (barrier) 178 that encloses the medicinal agent 180. For purposes of providing a concrete example, it is contemplated that the agent 180 is an insecticide to reduce incidence of insect activity (e.g., to ward off mosquitos, fleas, ticks, flies, etc.). Other agents can be used. These include, without limitation, hormones, vaccines, nutrients, vitamins, fluids, analgesics, antibiotics, etc.

The reservoir 172 is shaped as an internal cylinder with annular sidewalls 182 supported by a base support surface 184. This forms an internal cylindrical recess that supports the filled membrane 178 and protects the same from inadvertent rupture until needed. An opening 186 extends through the base support surface 184. It follows in this example that the opening 186 serves as the application mechanism 176 from FIG. 7.

A piezoelectric transducer (PZT) element 188 corresponds to the actuator 174. Upon activation, the PZT element 188 initiates high frequency vibrations that are sufficient to impinge upon the membrane 178 and rupture the same. This allows the agent 180 to flow out of the membrane from the reservoir and through the opening 186 to contact the inner ear surface 114A of the animal. In this way, the agent is spread via conventional mechanisms (as with other topical insecticides) across the skin and/or hairs of the animal to coat the animal and result in a controlled application of the agent, as if a user had applied the agent using conventional manual means.

Figure 8C:
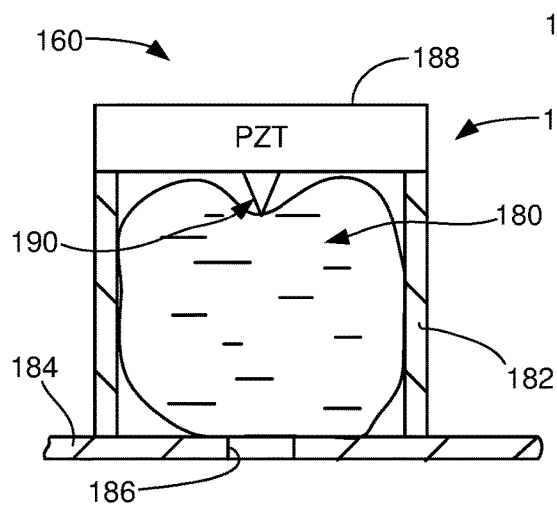

FIG. 8C shows the dispenser having a similar configuration as in FIG. 8B, except that a rupture mechanism 190, such as in the form of a sharpened plunger element, is affixed to the PZT element 188. In this way, activation of the PZT element forces the rupture mechanism 190 against and through the membrane 178, allowing the pharmaceutical agent to flow through the opening 186 as before.

Figure 8D:
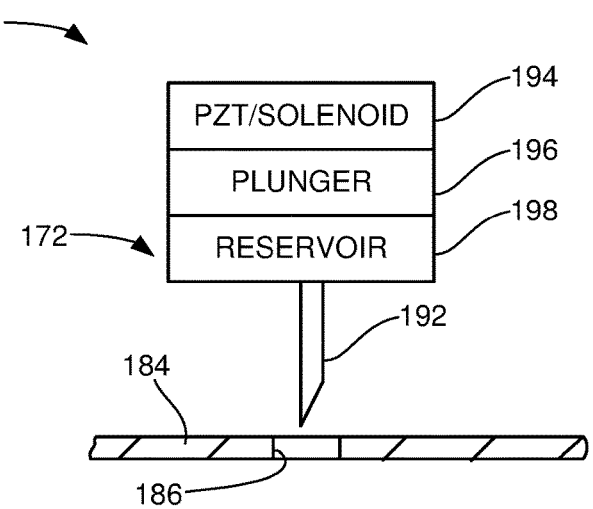

FIG. 8D shows yet another configuration for the dispenser 160. In this case, a hypodermic syringe (needle) 192 or similar mechanism extends through base plate 184 and is advanced, via operation via a PZT or solenoid mechanism 194 and plunger 196, to operate to inject the agent from reservoir 198 into the animal, in a manner similar to a conventional hypodermic syringe mechanism. It will be appreciated that other arrangements can readily be used as desired to administer the desired agent to the animal. These arrangements include, without limitation, to a door/port that is opened as a result of the actuation of the actuator 174, etc.

Figure 8E:
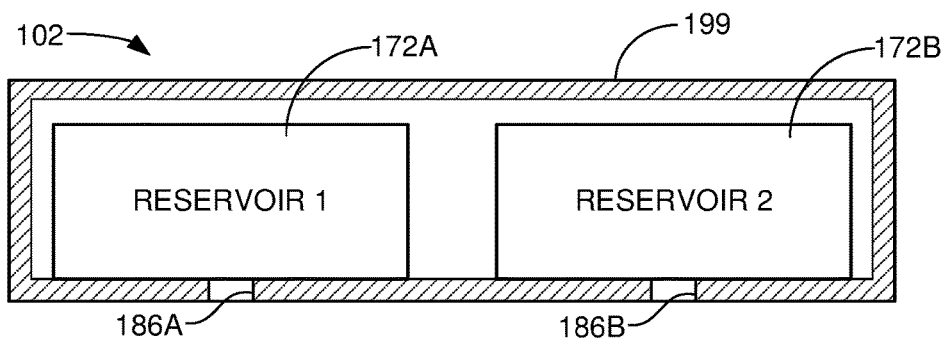

FIG. 8E is a schematic, cross-sectional representation of the tag 102 in accordance with further embodiments. The diagram illustrates first and second internal reservoirs 172A, 172B (denoted as Reservoir 1 and Reservoir 2) and corresponding first and second administration apertures 186A and 186B. While only two reservoirs are shown, any number of reservoirs and associated control elements can be provided as required. The reservoirs 172A, 172B, as well as other operative elements of the tag 102, are encapsulated within a rigid housing 199. Separate actuators (not shown) can be used to open the reservoirs, and administering mechanisms can include the apertures 186A and 186B as well as other elements as required (not separately shown) to administer the contents of the respective reservoirs 172A, 172B.

Figure 9:
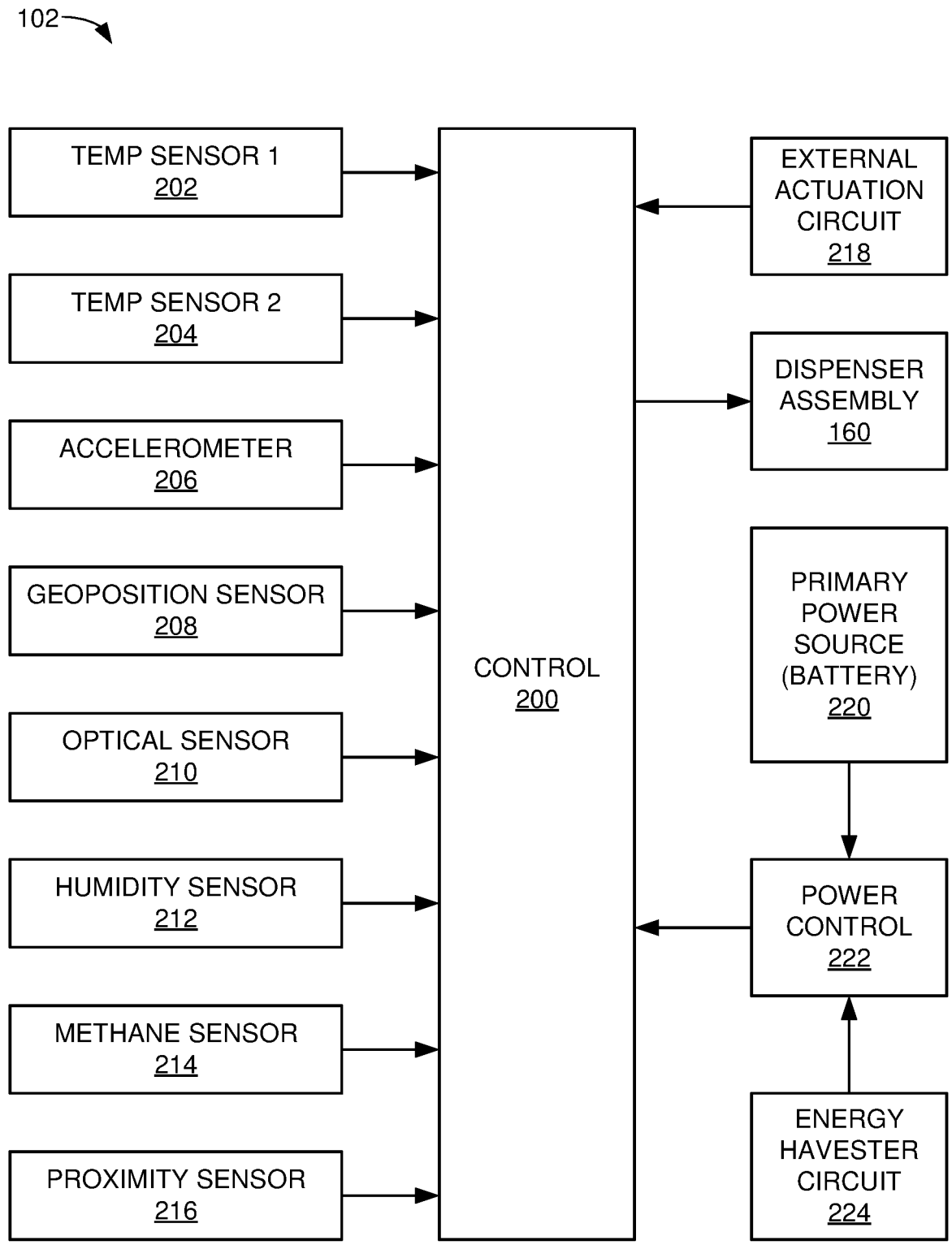
FIG. 9 is another functional block representation of the tag assembly in accordance with further embodiments.

FIG. 9 is another functional block representation of the tag assembly 102 in further embodiments. A main controller circuit 200 provides top level control of the tag 102. As discussed above, the main controller circuit 200 can be realized in a number of ways including but not limited to one or more programmable processors that execute programmable instructions (e.g., firmware) stored in a local memory. Additionally or alternatively, the main controller circuit 200 can be realized using one or more hardware circuits (including a state machine, an FPGA, etc.). Regardless of configuration, the controller circuit 200 receives a number of sensor inputs from various sensors, including a first temperature sensor 202 (such as one that measures an outer ear temperature of the animal), a second temperature sensor 204 (such as one that measures ambient temperature adjacent the animal), an accelerometer 206, a geoposition sensor 208, an optical sensor 210, a humidity sensor 212, a methane sensor 214 and a proximity sensor 216 (which may indicate proximity to another tag or other elements of the system).

An external actuation circuit is represented at 218. This can include circuitry that activates one or more of the dispenser assemblies 160 based on one or more sensor inputs from the sensors shown in FIG. 9, or from an external signal issued by a user via one or more of the elements shown in FIG. 1. In this way, the agent can be administered automatically based on sensor inputs; for example, if the accelerometer indicates a high level of agitation by the animal, this may indicate the presence of annoying insects, enabling the system to administer the agent. In another example, a user may determine that it is a suitable time to administer the agent, in which case a signal is forwarded to the tag to activate the actuator as described above. In yet another example, a combination of sensor indications may be used to diagnose a particular health state of the animal, resulting in automated or user directed activation of the dispenser assembly. An administration decision for a first animal can be used as the basis to proceed with an administration of the agent to other associated animals.

It will be appreciated that electrical power will generally be required to activate the various electrical and mechanical aspects of the tag assembly 102. To this end, a primary power source 220, such as a battery, may be used to supply electrical power. This can be supplied to a power control circuit 222 to supply electrical power to the remaining portions of the tag. In further embodiments, an energy harvester circuit, such as a solar collector array, a mechanical energy collector, etc., can be used to recharge the battery or supply further power to the tag, as desired.

Figure 10:
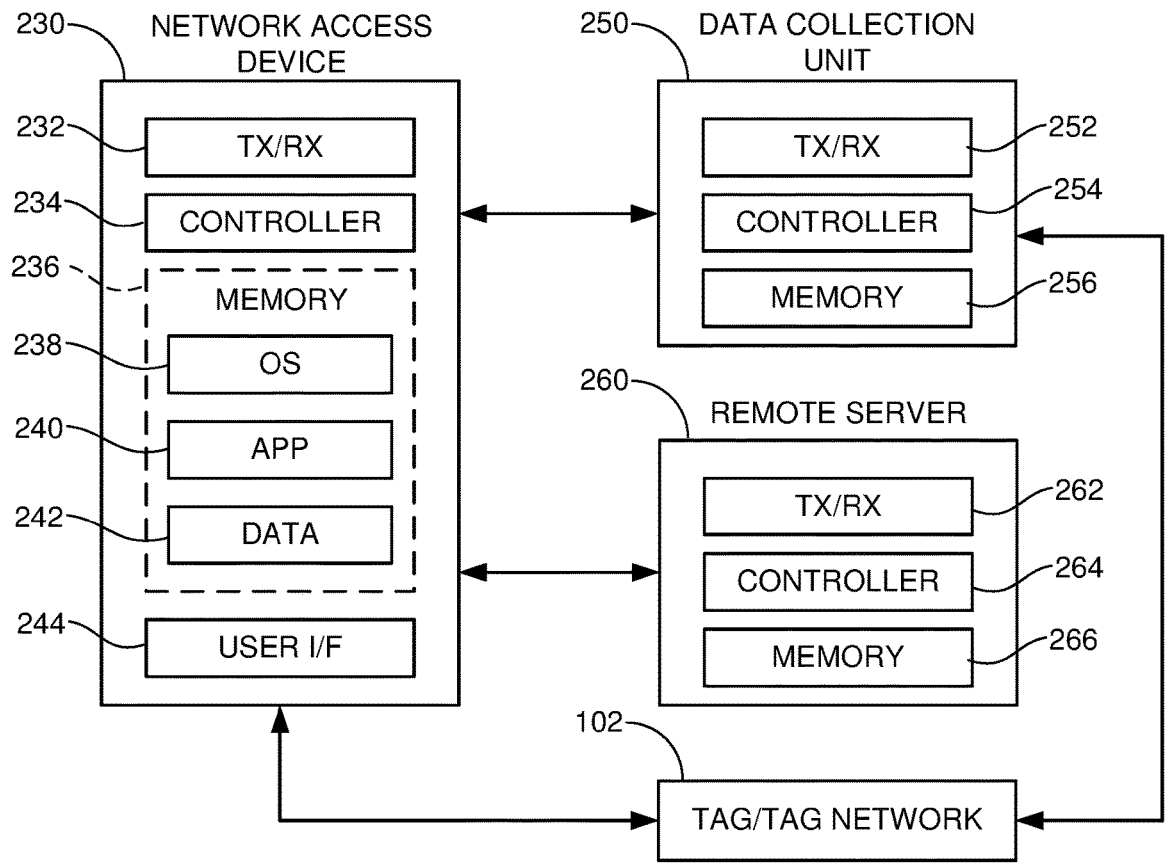
FIG. 10 shows aspects of the system of FIG. 1 in greater detail in accordance with some embodiments.

FIG. 10 shows another representation of the system 100 of FIG. 1 in greater detail. This diagram shows various elements that can interact to exchange information among the various components in the system, including the issuance of administration commands to a selected dispenser assembly 160.

A network accessible device 230 generally corresponds to the network accessible device 106 shown in FIG. 1, and can take any number of suitable forms of user (client) devices including a smart phone, a tablet, a laptop, a computer, etc. The device 230 includes TX/RX circuitry 232, a controller circuit 234 and memory 236. The memory stores various programming instructions and data structures including an operating system (OS) 238, an application program (app) 240 configured to enable communications with the other devices in FIG. 10, and data 242 collected from the tag(s) and other devices as required. A user interface (I/F) 244 includes a suitable graphical user interface such as a touch screen display, keyboard, etc. to enable the user to interact with the other devices. Other features may be included as well including power supply, audio/video recording features, etc. that may be user selectable as desired.

A data collection unit 250 generally corresponds to the data collection unit 104 in FIG. 1, and may be a stationary element positioned at a suitable location at which the animals congregate (e.g., near a watering or feeding location, in a barn, a milking station, etc.). It is contemplated, although not necessarily required, that the data collection unit 250 will automatically establish communications and data exchanges at such times that tag assemblies 102 come into range. In this way, data groupings can be cached and uploaded, commands can be cached and downloaded, etc. As noted above, the data collection unit need not be stationary; other configurations provide a mobile data collection unit, including but not limited to the drone-based collection system 108 of FIG. 1. Data collection and exchanges, as well as command data transfers, can be carried out using these and other platforms accordingly.

The data collection unit 250 includes a TX/RX circuit 252 that broadcasts signals in a relatively small area (e.g., transmission range via the Bluetooth specification, etc.) to detect both the tags 102 and the device 230 and automatically synchronize with these components. A controller circuit 254 and associated memory 256 may be used to direct data, command and status upload/download operations. It is contemplated that the data collection unit may be associated with or incorporated into other equipment, such as a milking machine in a dairy farm, etc.

A remote server 260 can correspond to the server 108 in FIG. 1 and can communicate either directly to the data collection unit or the respective network accessible devices as desired. These communications can be carried out directly or over an intervening network, such as the network 110 in FIG. 1. The server 260 can include TX/RX circuitry 262, a controller circuit 264 as one or more programmable processors and memory 266. In some cases, history data is archived by the memory 266 to provide long term storage and analysis capabilities of the data. Data analyses and reporting can be performed on the data at both the device 230 and server 260 levels as required. In some cases, the server can maintain history data regarding administration schedules and either direct the operation of the dispenser assemblies or can provide recommendations to the user via the network accessible device 230 about appropriate times to activate the administration of various agents. Any number of network interconnections can take place as desired, including but not limited to Bluetooth, near-field communications, cellular data networks, wireless networks, local and wide area networks, drone based networks, satellite-based networks, etc.

Figure 11:
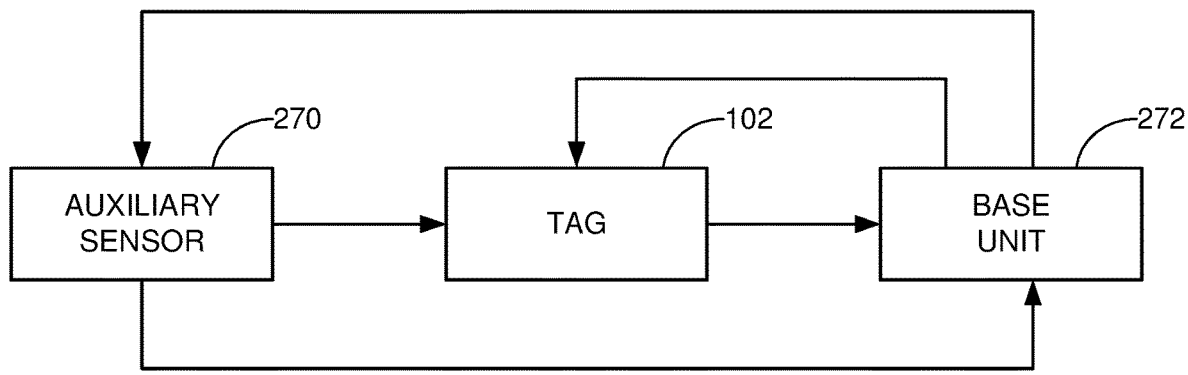
FIG. 11 illustrates the use of an auxiliary sensor in accordance with further embodiments.

FIG. 11 shows another arrangement of the system in which one or more auxiliary sensors 270 are utilized in conjunction with the tag assembly 102. The auxiliary sensor 270 is a physically separate sensor that is attached to or otherwise disposed proximate the animal. Examples include sensors that attach to an external portion of the animal body (e.g., a leg, a tail, etc.), sensors that are ingested (e.g., swallowed), sensors that are stationary and are not attached to the animal, and so on. These specially configured sensors may be configured to transmit parametric data using a short range wireless communication protocol. As before, various commands and data can be exchanged among these various elements.

The transmitted data from the external (auxiliary sensor) may be forwarded to the tag 102 and/or to a base unit 272 as described above. If the data are transmitted to the tag 102, the tag in turn may transmit, to the base unit 272, data obtained by the auxiliary sensor 270 as well as data obtained by the various sensors of the tag 102. Other data transfer paths are contemplated as well. Data may be transferred directly from the auxiliary sensor 270 to the base unit, and this data may bypass the tag 102 entirely. Yet other data transfers, including control signals, may be directed by the base unit 272 to the respective auxiliary sensor 270 and the tag 102.

Figure 12A:
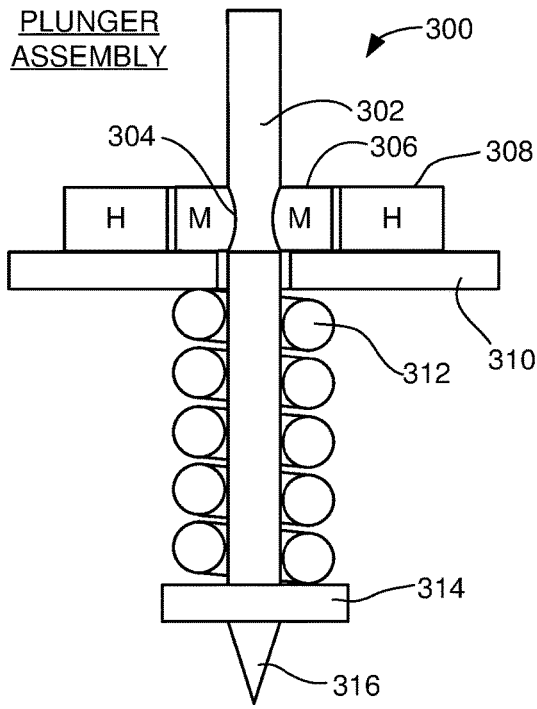
FIGS. 12A and 12B illustrate a plunger assembly useful as part of the dispenser assembly in accordance with further embodiments.
Figure 12B:
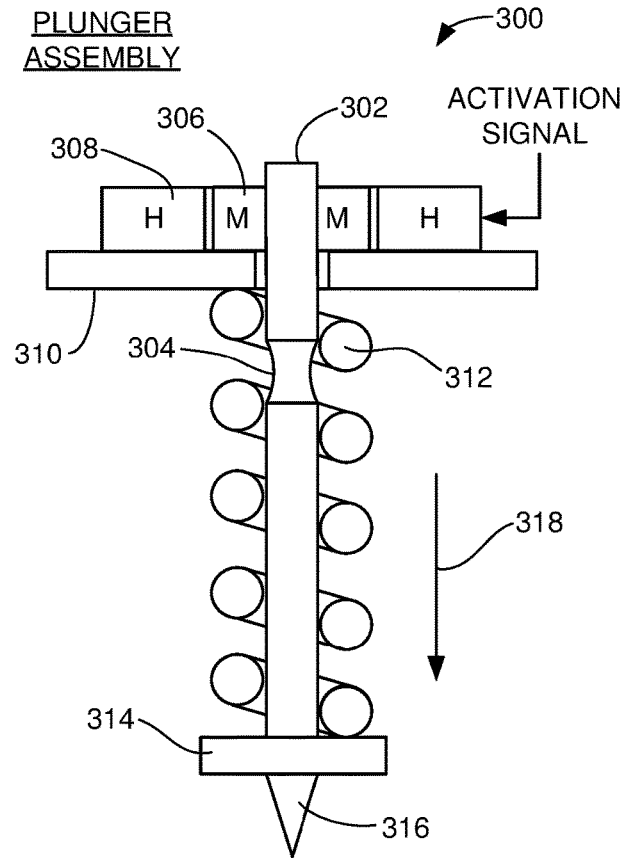

FIGS. 12A and 12B illustrate a plunger assembly 300 that can be incorporated into the tag 102 to administer a suitable pharmaceutical agent as discussed above. The plunger assembly 300 is similar in some ways to a traditional "turkey indicator" mechanism of the type arranged to provide a visual indication that a turkey (or other poultry dish) has achieved a desired internal cooking temperature.

As shown in FIG. 12A, the plunger assembly 300 includes a central shaft 302 of a suitable rigid material, such as metal, injection molded plastic, etc. the shaft 302 may be substantially cylindrically shaped and includes a detent region 304 along an upper medial portion of the shaft.

A retention ring 306 is arranged to normally fill and contactingly retain the detent region 304. The ring 306 may be formed of a suitable metal or metal alloy with a melting temperature at a selected level. Other materials can be used. A heater assembly 308 surrounds the ring 306 and is adapted to apply heat to the ring to induce a change in state (e.g., transition from a solid to a molten state) responsive to an input signal from associated circuitry (see e.g., FIGS. 5 and 9). This input signal, which is identified as an activation signal, can comprise or be based on a control signal used to initiate a dosage event.

An internal support structure 310 is disposed below the ring 306 and the heater assembly 308, and is arranged to permit sliding passage of the shaft 302 therethrough as shown. A coiled spring 312 is arranged to be compressed between the support structure 310 and an annular flange 314 at a distal end of the shaft 302. As desired, a puncturing tip 316 extends from the annular flange. In the arrangement of FIG. 12A, stored energy in the spring 312 presses between the stationary support structure 310 and the flange 314, and this configuration is maintained by the interlocking arrangement of the solid metal ring 306 with the detent 304.

At such time that it is desired to release this stored energy, an input activation signal (indicated by arrow 318) is supplied to the heater assembly 308. This is shown in FIG. 12B. In some cases, this may be the application of a flow of electrical current from a stored source (e.g., battery, capacitor, etc.) sufficient to cause the heater assembly 308 (which may be, for example, a resistive element) to melt or otherwise soften the ring 306. At this point, the retention force between the ring 306 and the detent 304 of the shaft 302 will be reduced sufficiently to enable the spring 312 to displace the flange 314 and tip 316 downwardly, as indicated by arrow 318. As discussed above, this actuation may result in the puncture of a membrane containing the pharmaceutical agent, allowing administration of the same to the animal. Other resulting actuations as a result of the release of the stored energy in the spring 312 are contemplated and will readily occur to the skilled artisan.

Figure 13A:
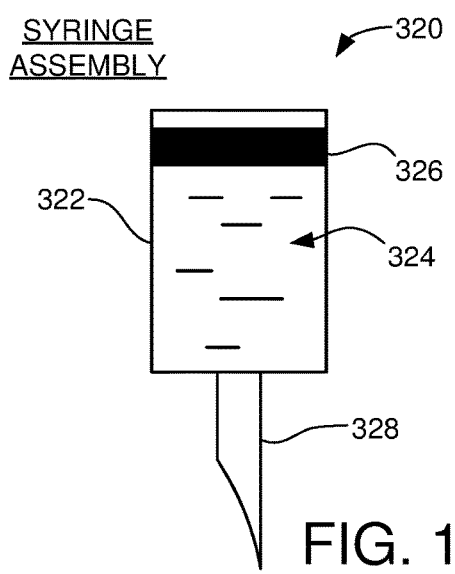
FIGS. 13A and 13B show a syringe assembly useful as part of the dispenser assembly in accordance with further embodiments.
Figure 13B:
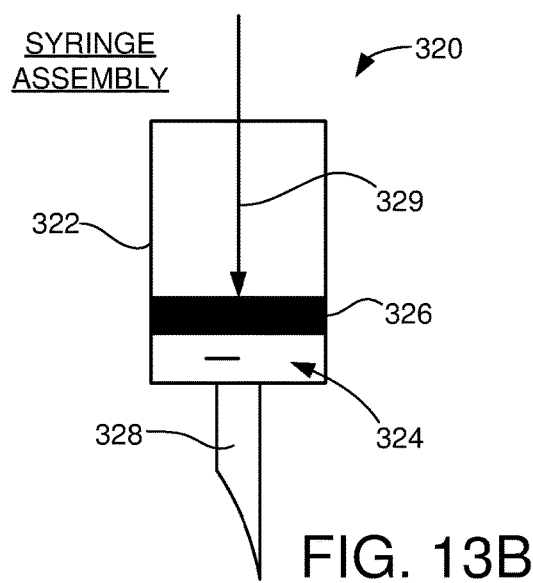

FIGS. 13A and 13B show a syringe assembly 320 that can be incorporated into the dispenser assembly of the tag as discussed above. In some cases, the syringe assembly 320 can be incorporated into an activation system such as discussed above in FIGS. 12A and 12B. In other cases, different types of activation systems can be used.

The syringe assembly 320 includes a reservoir 322, which can be a cylindrical repository for a selected amount of pharmaceutical agent 324. A fluidic-tight, sliding plunger 326 can be positioned at an upper end of the reservoir 322. A syringe 328 (e.g., hollow needle-type instrument) can be arranged at an opposing, second end of the reservoir 322, as shown. A downwardly directed force, indicated by arrow 329 in FIG. 13B, can be used to advance the plunger 326 within the reservoir 322 to administer the agent 324. As desired, a separate force (not shown) can further cause advancement of the syringe 328 into the body of the animal to introduce the agent into said body.

Figure 14:
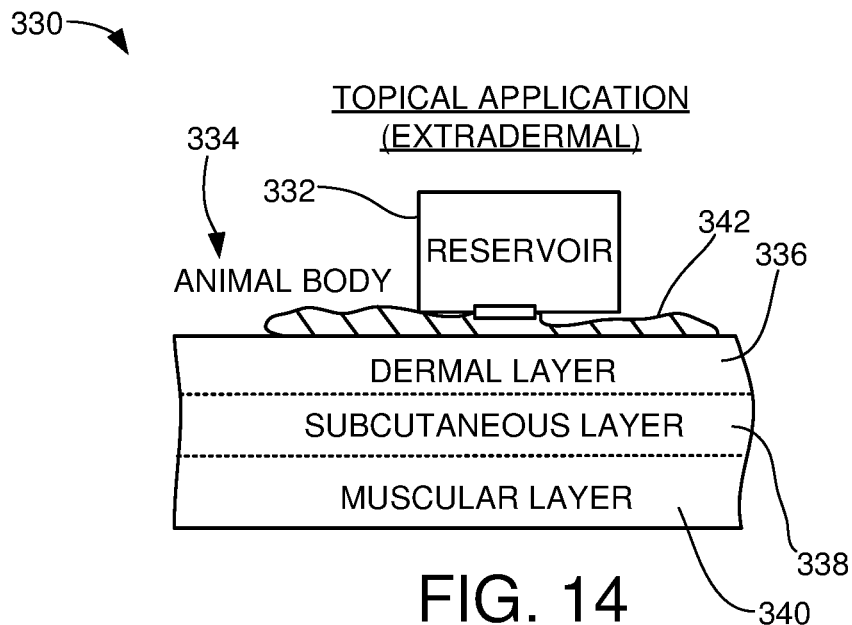
FIG. 14 illustrates a topical (extradermal) application system in which a pharmaceutical agent is applied topically to an external service of an animal body in accordance with some embodiments.

FIG. 14 shows another administration system 330 that can be used in some embodiments to provide topical (extradermal) application of a pharmaceutical agent to an animal in accordance with the foregoing discussion. The system 330 includes a reservoir 332 that is placed adjacent an animal body 334. The animal body 334 includes a number of tissue layers including a dermal (skin) layer 336, a subcutaneous (fat) layer 338, a muscular layer 340, etc.

In FIG. 14, application of a suitable force upon the reservoir 332 induces a flowing of a pharmaceutical agent 342 onto an exterior surface of the dermal layer 336, as shown and aforedescribed above.

Figure 15:
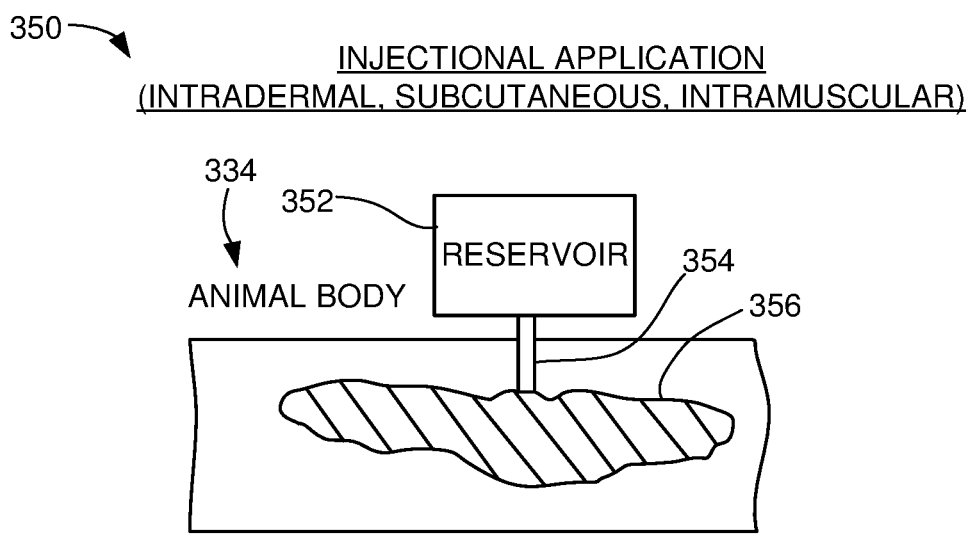
FIG. 15 illustrates an injectional (intradermal, subcutaneous and/or intramuscular) application system in which a pharmaceutical agent is applied into an animal body in accordance with other embodiments.

FIG. 15 provides yet another administration system 350 that can be used in further embodiments to provide an injectional application of a pharmaceutical agent to an animal in accordance with the foregoing discussion. As before, the system 350 includes a reservoir 352 placed adjacent the animal body 334. However, in this case an injection mechanism 354 (such as the syringe 328 in FIGS. 13A and 13B) penetrates at least a selected one of the dermal, subcutaneous and/or muscular layers 336, 338, 340 (FIG. 14) in order to introduce a pharmaceutical agent 356 into the animal body 334. While not separately shown, in some cases the injection mechanism 354 may provide an intravenous injection (e.g., into one or more veins of the circulatory system of the animal). In other cases, the agent may be introduced into a tissue portion of the animal.

Figure 16:
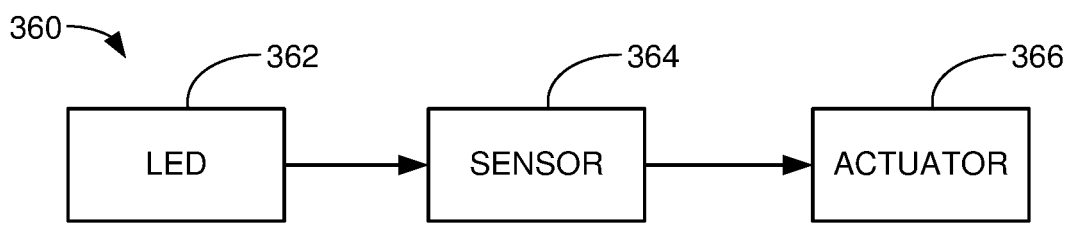
FIG. 16 is a functional block diagram illustrating another activation arrangement for the tag assembly in some embodiments.

FIG. 16 is a functional block diagram of an activation system 360 that can be used in some embodiments to initiate and signal activation of a dispenser assembly in accordance with further embodiments. The system 360 includes a light emitting diode (LED) or other light source 362, an optical sensor 364 and an actuator 366.

The LED 362 can be triggered remotely by an external device through application of a control signal, such as from a selected user network accessible device 106 (see FIG. 1). The LED 362 can be incorporated into the body of the tag assembly 102, and can convey useful information to the user; even at a distance, status information can be visually conveyed from the tag via the LED (e.g., power on, status information, etc.) to a human observer or other detection mechanisms. While not limiting, the LED can be a single color (wavelength) or multi-color unit. The LED can further be controlled to provide a consistent (solid) output, to flash, etc. under different conditions. In this way, the LED can provide, at a glance, a status of an animal to which the tag, which incorporates the LED (or other light source), is attached.

This LED feature can be particularly useful when a group of animals (e.g., a herd) are grouped together, as the LEDs can be visually checked to signify that all of the tags are working, the animals are in good condition, and so on. For example, if one animal is in a distressed condition (e.g., elevated temperature, excessive agitation, etc.), that particular animal might be supplied with an LED output that is distinguishable, from a visual standpoint, as compared to the rest of the animals in the herd. Similar animal information may also be conveyed to the user's network accessible device, but the LED will allow the user to immediately identify the animal in question from among the herd group.

In FIG. 16, the system 360 further utilizes the output from LED 362 to activate the dispensing of a dose of pharmaceutical agent to the associated animal. To this end, the output from the LED 362, which is configured to shine outwardly from the tag, is also detected by the sensor 364, which is incorporated within the tag. The sensor 364 may detect all activations of the LED, activations of the LED in a particular flashing sequence, activation of a particular color from the LED, etc.

When activation of the LED 362 is intended to initiate the dispenser assembly, the sensor 364 detects this activation of the LED 362 and provides an output that is directed to the actuator 366, which in turn operates as described above to initiate dispensing of the pharmaceutical agent. In this way, visual indication can be supplied to an observer that a dosage is being supplied to the selected animal. This system also allows the observer to confirm that dosages are being provided to each of the various members of the herd in turn, if a group activation is desired.

Figure 17:
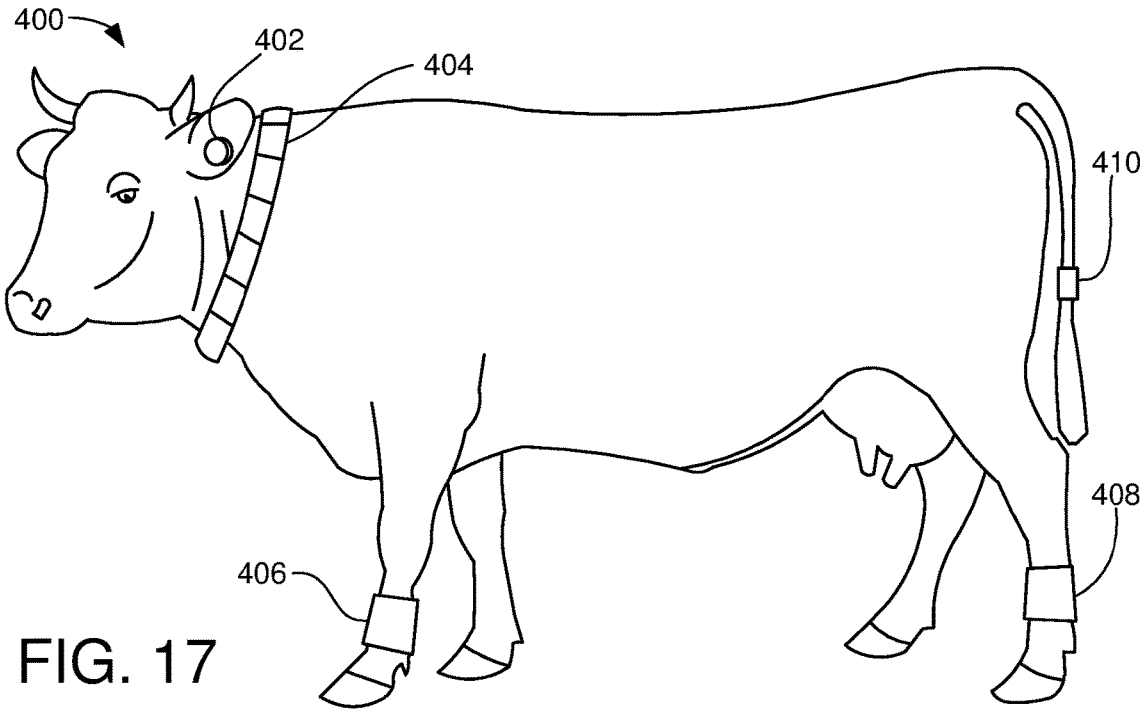
FIG. 17 illustrates another animal (e.g., a cow) having various sensor and application systems arranged in accordance with yet further embodiments of the present disclosure.

FIG. 17 schematically depicts another animal 400, characterized as a cow. The cow 400 has a number of tag-style assemblies attached thereto, including an ear tag 402, a necklace 404, leg bracelets 406, 408, and a tail ring 410. Other arrangements can be used as desired. The various sensors, controls and dispenser assembly arrangements discussed above can be readily incorporated into these and other types of assemblies, as desired, in order to efficiently administer appropriate pharmaceutical agents to appropriate locations of the body of the cow. As noted above, these and other types of tags can be applied to other forms of animals as well.

Figure 18:
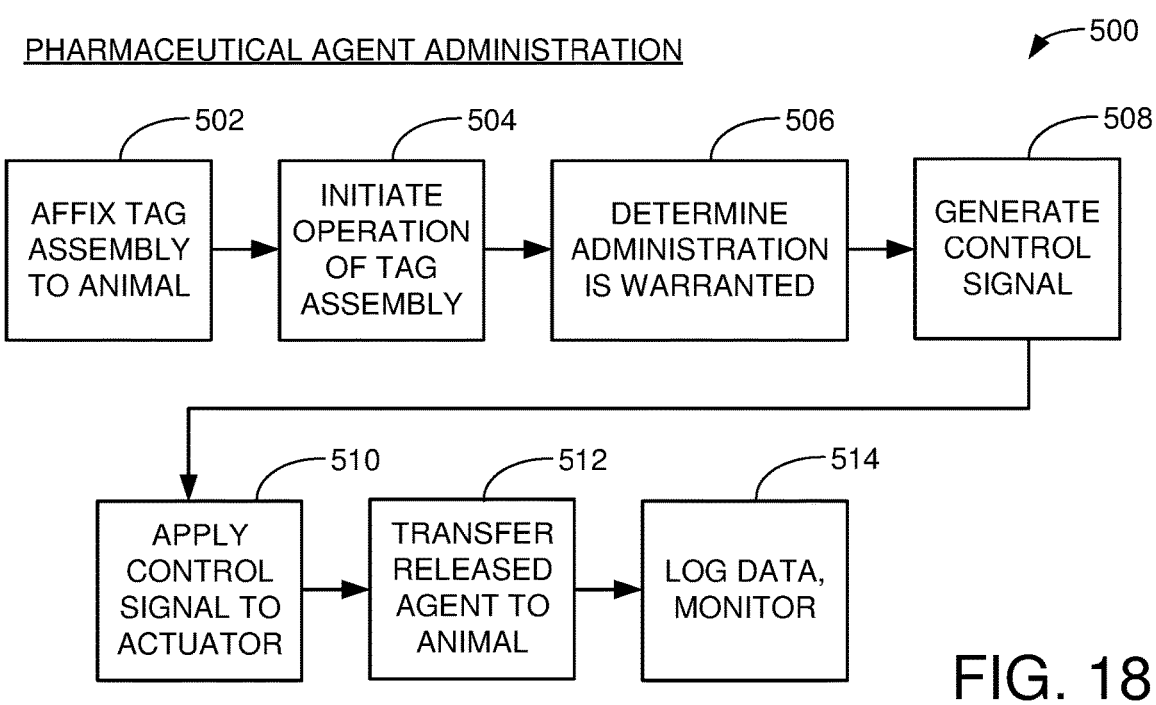
FIG. 18 is a flow diagram to illustrate application of the pharmaceutical agent in accordance with various embodiments.

FIG. 18 is a flow diagram 500 to summarize various steps that can be carried out to administer a pharmaceutical agent to an animal in accordance with the foregoing discussion. The various steps are merely illustrative and can be modified, rearranged, appended, etc. based on the requirements of a given application.

Block 502 depicts the affixing of a tag assembly to the animal. The tag assembly can take the various forms discussed above, including the ear tags 102, 402, the necklace 404, the leg bracelets 406, 408, the tail ring 410, etc. Operation of the tag assembly is initiated at block 504. This can include the transmission of a signal to the installed tag. At this point, the tag assembly carries out various native functions described herein, including monitoring operations regarding the tagged animal. Such operation may be carried out under the direction of the controller 142, 200, and can include commands issued by remaining aspects of the system 100 (see FIG. 1).

At some point (either upon initialization or at a future point in time), a determination is made that administration of a dose of the pharmaceutical agent is warranted, as indicated by block 506. This can happen as a result of the initiating of the operation of the tag, or can be commanded at a subsequent time, either automatically or as a result of a user input.

In response to the determination that an administration event should be carried out, a control signal is generated at block 508. As described above, the control signal may be generated by a control circuit that is internal to the tag assembly or external to the tag assembly. The control circuit can include, without limitation, the controllers 142, 200 in FIGS. 5, 7 and 9; the controllers 234, 254 and/or 264 in FIG. 10; the base unit 272 in FIG. 11, etc. The control circuit may utilize a programmable processor, but other forms of circuits can be alternatively used as desired. In some cases, a first control signal will be transmitted wirelessly to the tag assembly, and in response, a second control signal will be generated in response to the first control signal. The generation of the control signal can be an automated event, or directed by a human user.

As shown by block 510, the control signal is applied to an actuator of the tag assembly. The actuator is configured as described above to release the agent from an associated reservoir of the tag assembly in response to receipt of the control signal. The released agent is thereafter transferred to the animal, block 512. Thereafter, data associated with the animal are logged, and behavior of the animal is monitored, block 514. The data can include date/time/dosage information associated with the administration, as well as data showing any changes in behavior, etc. as a result of the application. While the flow diagram concludes at this point, it will be appreciated that additional administrations can be subsequently carried out by returning to block 506.

In view of the foregoing discussion, a number of use cases will now be presented to further illustrate various manners in which the disclosed subject matter can be utilized. It will be appreciated that these are merely illustrative examples and that other use cases are contemplated and will be immediately apparent to the skilled artisan based on the present disclosure. For simplicity of discussion, each of these cases will contemplate application of an insect repellant to a cow (e.g., a female bovine animal such as illustrated in FIGS. 2 and 16) using an ear tag assembly. However, the use cases can be easily modified to address other operational environments (e.g., a male bovine animal, a juvenile bovine animal, other forms of domesticated and wild animals, other pharmaceutical agents, etc.). The use cases are contemplated as involving integration with an overall data collection and analysis system such as presented above in FIG. 1.

Use Case 1—Scheduled Administration

This first use case contemplates a scheduled administration of the insect repellant to the cow on a regularly scheduled basis. For example, assuming that a particular season is known to produce flying insects of the type likely to produce agitation of the cow (e.g., flies, mosquitos, etc.) that lasts for eight (8) weeks, then the system may be configured such that the tag assembly applies one dosage every two (2) weeks, for a total of four (4) treatments.

The schedule would be based on the effective duration of each treatment. For example, if the repellant were effective in providing relief to the animal for a four (4) week period, then it is contemplated that only two (2) administrations may be required, the first at the beginning of the season and the second mid-way through the season. In this way, the cow can be safely and effectively administered a suitable repellant on a predetermined, controlled basis autonomously without the need for human intervention. The internal control circuitry of the tag (see e.g., controller circuit 148 in FIGS. 5 and 200 in FIG. 9) can be configured to track the intervening time between doses, and schedule and administer the same at the appropriate times without the need for the application of external signals to the tag assembly.

Use Case 2—Sensor-Based Administration

This second use case contemplates the same eight (8) week season for the flying insect pestilence. However, after an initial administration of a first dose, behavior of the cow is monitored using the sensors of the tag assembly to determine whether behavior performance remains within acceptable limits. It is likely that, even with the application of an insect repellant the cow will still exhibit behavior indicative of the presence of the flying insects (e.g., head shaking, movement of tail, walking, running or jumping behavior, etc.). Care will be taken as part of the analysis to distinguish movements that are interpreted as being due to insect annoyance as compared to other reasons (e.g., fertility, illness, etc.). Heuristic analyses can be used to develop a profile that indicates levels of acceptable and unacceptable behavior. In this way, filtering can be used so that a distinction can be made whether it is appropriate to administer further dosages of the repellant to the animal.

If the observed behavior of the cow is within acceptable norms, nothing will be done other than to continue monitoring this behavior. However, if excess agitation is noted, the tag assembly may proceed (such as via the onboard controller circuitry) to activate another application of the insect repellant. Care should be taken to not overdose the animal, so protocols can be used that maximum dosages are not exceeded over a given time period. Nevertheless, it can be seen from this second use case that certain animals may be exhibiting increased agitation and therefore may be permitted to receive additional relief at an accelerated schedule. Comparison of data from a herd of cows can be used as part of this determination. Statistics will be gathered and tracked to determine overall status of the heard using the traceability protocols of the overall system (see e.g., FIGS. 1, 5 and 9-10).

In some configurations, the scheduled application of Use Case 1 can be combined with the specific administration of Use Case 2, so that normally the animals are dosed on a regular basis, but additional applications are available and can be applied to individual animals on an as-needed basis. It is also possible in some cases that a regular schedule may be initially established, but adherence to the schedule is based on individual animal behavior. In this alternative, some animals may receive dosages at the scheduled times, some animals may receive fewer dosages at a lower frequency because the animals do not appear to be bothered by the environmental conditions, and yet other animals may receive more dosages at a higher frequency due to heightened observed sensitivity. Various parameters (e.g., milk production, geotracking, temperature, etc.) can be used to individually evaluate the status of each animal, and identify an appropriate protocol therefor.

While this use case contemplates using the sensors that are in the ear tag assembly affixed to the cow, it will be apparent that other sensors can be used instead or as part of the determination process. Such sensors can include sensors located on other parts of the cow (e.g., see FIG. 16), remote sensors (including stationary sensors near feed troughs, watering locations, etc.), portable sensors (including sensors mounted to portable drones, human carried sensors, animal carried sensors, etc.), and so on.

As noted above, the system can operate to automatically dispense the insecticide (or other pharmaceutical agent) in response to the sensor indication(s). Alternatively, a notification can be supplied to a user, such as a user of the network accessible device (106, FIG. 1). The user can then be given the option to proceed with administration of the dose. By activating an available option on the interface of the device, a control signal can be forwarded to the respective tag to initiate the dosage treatment. In some cases, the user may be given the option to proceed with activation of other animals in the herd at this time as well, in which case if the user decides to so proceed, each of the other animals will likewise be treated. This can be visually confirmed both via the device as well as by the LEDs in FIG. 16.

Use Case 3—Server-Based Administration

Use Case 3 is similar to those described above, but this case utilizes the full power of the data collection and control system in order to determine optimum times and, as required, dosage levels to apply to the cow. Information that can be included in this determination include weather reports, governmental data, statistical analysis from other mechanisms (including insect detection and concentration systems from external sensors and reporting authorities), and so on.

The basic principle is that the status of the cow individually and the status of the herd overall are tracked and used to determine an optimized dosage schedule for the respective animals in the herd, based on up-to-date information available from any number of available sources. Animal aging, history, status (e.g., whether the cow is currently pregnant or has recently given birth, etc.) and other factors are utilized in tailoring an appropriate dosage schedule. Real-time monitoring is provided to allow adaptive changes in the dosage application and scheduling.

This embodiment contemplates an option where a user, observing the behavior of the herd and/or relying on data reported by the system, can utilize a device, such as one of the network accessible devices 106 in FIG. 1 (e.g., a smart phone, a tablet, a computer, etc.) to transmit a control signal to the associated tag assembly of the associated cow to initiate, either immediately or on a scheduled basis, an application of an appropriate dosage of the repellant. These and other actions are logged as part of the traceability program, so that a record is retained of the pharmaceutical administration (as well as all other actions taken concerning the cow or other animal).

While these and other embodiments have considered each dosage available in each reservoir to be nominally the same volume, it is alternatively contemplated that different dosages (e.g., smaller amounts and larger amounts) can be available. In this way, the actual amount of applied pharmaceutical agent can be administered to an animal on an as needed basis. Further, it is contemplated that, based on the reservoir, actuator and delivery mechanism configurations, all of the available pharmaceutical agent can be administered at once, or a partial dose can be supplied, leaving additional agent available for application at a later time from the same reservoir.

It has been largely contemplated based on the foregoing discussion that the pharmaceutical agent will be in a liquid form, but such is not necessarily required. A solid, low viscous and/or tablet material could alternatively be used while still carrying out the operations of the disclosed subject matter. For example, a waxy-type, semi-solid block/cylinder of material could be advanced using a plunger, screw drive and/or squeeze type applicator (similar to a solid deodorant applicator, etc.) to apply the pharmaceutical agent to the animal.

The embodiments of the present disclosure provide solutions that stave off problems before they become catastrophic. It has been found that the annoyance of flying insects, for example, can have deleterious effects upon animals that can severely impact their health and welfare. Animals have been known to exert themselves to exhaustion and even death trying to escape the plague of insect infestations. To a lesser degree, the productivity of animals (measured in any number of ways including milk production, weight gain, temperature, activity, etc.) can be severely limited based on environmental conditions. These and other real world conditions are addressed by providing the autonomous application of beneficial pharmaceutical agents that can provide relief from these and other effects.

Any number of wireless communication protocols may be used as required to communicate data between the various operative elements of the system. Without limitation, these can include RFID, NFC, Bluetooth, Wi-Fi, ZigBee, cellular, server specific protocols, etc. Conformance can be made with various industry established communication standards including but not limited to ISO 18000, ISO 14443, IEEE 802.11, IEEE 802.15, the Bluetooth Special Interest Group (SIG), etc. The same communication protocol can be used throughout the system or different protocols can be used to handle communications between individual pairs of devices as required (see e.g., FIG. 1).

It will now be appreciated that the various embodiments presented herein have a number of advantages and benefits over the existing art. The automated administration of pharmaceutical agents can be carried out based on user inputs sent electronically to the tags, and/or based on sensor readings by the tag (either processed independently at the tag level or sent upstream to another device such as the local devices or the remote server). Any number and types of pharmaceutical agents can be administered. In some cases, the agents can be administered automatically on a predetermined time schedule (e.g., every 2 weeks); in other cases, the agents may be administered based on sensor indications regarding the health of the animal as collected directly or indirectly by the tag assembly. Another advantage is traceability; the tag assembly enables a full history of the animal, including all actions taken therewith, all geopositions of the animal during its lifecycle, all health status and other information associated with the animal, and all pharmaceutical agents applied to the animal, can be easily collected and verified.

While the various embodiments have been described in terms of domesticated livestock animals, particularly cattle, the embodiments can be readily adapted for any number of other applications including being used with substantially any form of animal, including domesticated or wild mammals, humans, etc.

It is to be understood that even though numerous characteristics and advantages of various embodiments of the present disclosure have been set forth in the foregoing description, this description is illustrative only, and changes may be made in detail, especially in matters of structure and arrangements of parts within the principles of the present disclosure to the full extent indicated by the broad general meaning of the terms wherein the appended claims are expressed.

What is claimed is:

1. A tag assembly for attachment to an animal, comprising:
    a reservoir within the tag assembly that retains a pharmaceutical agent;
    an actuator configured to open the reservoir responsive to a control signal from a control circuit; and
    an application mechanism configured to, responsive to the actuator, facilitate a transfer of the pharmaceutical agent to the animal to administer the pharmaceutical agent thereto.

2. The tag assembly of claim 1, wherein the pharmaceutical agent is an insecticide.

3. The tag assembly of claim 1, wherein the reservoir comprises a membrane that encloses the pharmaceutical agent, and the actuator ruptures the membrane to enable the flow of the pharmaceutical agent to the animal responsive to the control signal.

4. The tag assembly of claim 1, wherein the application mechanism comprises a hypodermic syringe which injects the pharmaceutical agent into an interior tissue or bloodstream of the animal.

5. The tag assembly of claim 1, wherein the actuator operates upon the reservoir to release the pharmaceutical agent therefrom responsive to the control signal being transmitted to the tag assembly by a separate network accessible device of a user.

6. The tag assembly of claim 1, wherein the actuator operates upon the user to release the pharmaceutical agent therefrom responsive to the control signal being generated from a sensor associated with the animal.

7. The tag assembly of claim 6, wherein the sensor is disposed within the tag assembly that includes the pharmaceutical agent.

8. The tag assembly of claim 6, wherein the sensor comprises at least a selected one of a temperature sensor or an accelerometer.

9. The tag assembly of claim 1, wherein a remote server monitors one or more sensor outputs from the tag assembly and sends a signal to the tag assembly via an intervening computer network to activate the actuator in response to a determined health state of the animal based on the one or more sensor outputs.

10. The tag assembly of claim 1, wherein the tag assembly is affixed to and extends through an ear of the animal.

11. The tag assembly of claim 1, wherein the control circuit comprises a programmable processor of the tag assembly.

12. The tag assembly of claim 1, wherein the actuator comprises a compressed spring which stores potential energy, the compressed spring released to advance a shaft responsive to the control signal, the shaft acting upon the reservoir to release the pharmaceutical agent.

13. The tag assembly of claim 1, wherein the pharmaceutical agent comprises a topical insecticide that is released onto an outer surface of the animal responsive to an accelerometer input from the tag assembly indicative of a heightened activity level of the animal suggestive of annoyance, of the animal, by insects.

14. The tag assembly of claim 1, wherein the reservoir is a first reservoir housing a first volume of pharmaceutical agent and the tag assembly further comprises a second reservoir housing a second volume of pharmaceutical agent, the first and second reservoirs independently activated to apply the respective first and second volumes of pharmaceutical agents at different times to the animal.

15. The tag assembly of claim 14, wherein the first and second reservoirs house the same type of pharmaceutical agent.

16. The tag assembly of claim 14, wherein the first reservoir houses a first type of pharmaceutical agent and the second reservoir houses a different, second type of pharmaceutical agent.

* * * * *